United States Patent [19]
Ogishima et al.

[11] Patent Number: 6,001,061
[45] Date of Patent: Dec. 14, 1999

[54] ULTRASONIC MEASUREMENT APPARATUS

[75] Inventors: Eiichi Ogishima, Otawara; Kazuya Akaki, Tochigi-ken, both of Japan

[73] Assignee: Kabushiki Kaisha Toshiba, Kawasaki, Japan

[21] Appl. No.: 09/037,921

[22] Filed: Mar. 10, 1998

[30] Foreign Application Priority Data

Jun. 5, 1997 [JP] Japan .................................. 9-147837

[51] Int. Cl.$^6$ ....................................................... A61B 8/00
[52] U.S. Cl. ......................... 600/440; 600/449; 600/443
[58] Field of Search .................................. 600/440, 442, 600/443, 449, 437

[56] References Cited

U.S. PATENT DOCUMENTS 5,553,620  9/1996  Snider et al. ........................... 600/440

Primary Examiner—Francis J. Jaworski
Assistant Examiner—Ali M. Imam
Attorney, Agent, or Firm—Oblon, Spivak, McClelland, Maier & Neustadt, P.C.

[57] ABSTRACT

At a measuring time, when at least one desired measurement category is selected from among a plurality of measurement categories associated with an ultrasonic image, at least one measurement item is selected from among a plurality of measurement items under the selected measurement category. Measurements corresponding to the selected measurement items are made sequentially. A title of those selected measurement items is inserted in a report. Since the title of those not-selected measurement items is not inserted in the report, there never occurs a situation in which the actually measured items and measurement results are buried in a vast number of measurement items, making it difficult to find them. That is, it is possible to minimize the number of pages and, by doing so, easily review the full actual measurement items one at a time on one screen or on one page and simply do this while being scrolled fewer times on a display screen or eye-scanning the pages of the report as required.

9 Claims, 6 Drawing Sheets

REPORT(1/2)　　TIS9.9 TIB9.9 TIC9.9 MI9.9
　　　　　　　　999　　　　　　96/05/11
　　　　　　　　A-HEART2　08:15:30AM
HT:175.0cm  BSA:1.77cm²
WT: 60.0kg  <ADULT>

☐ LV(SIMPSON)　　☐ DOPPLER MVA　　☐ AORTIC

| | | | | | | |
|---|---|---|---|---|---|---|
| LVLD | 54.5 (mm) | VP1 | -0.11 (m/s) | RVOTD | 69.6 | (mm) |
| VLAMD | 3.2 (cm²) | VM1 | -0.10 (m/s) | AOD | <32.2> | (mm) |
| LVAPD | 2.8 (cm²) | PHT1 | 240 (ms) | LAD | 55.4 | (mm) |
| LVLS | 28.3 (cm²) | MPG | 10.0 (mmHg) | AVD | 28.0 | (mm) |
| LVAMS | 1.2 (cm²) | VP2 | -0.13 (m/s) | ET | 1040 | (ms) |
| LVAPS | 2.0 (cm²) | VM2 | -0.09 (m/s) | | | |
| HR | 63 | PHT2 | 182 (ms) | LA/AO | <1.6> | |
| | | MPG2 | 20.1 (mmHg) | | | |
| | | AVD | 28.0 (mm) | | | |
| EDV | 12.8 (mL) | | | | | |
| ESV | 3.3 (mL) | MVA | 91.7 (mm²) | | | |
| SV | 9.5 (mL) | MVA2 | 125.0 (mm²) | | | |
| CO | 0.60 (L) | | | | | |
| EF | 0.74 | | | | | |
| SI | 5.4 | | | | | |
| CI | 0.34 | | | | | |

<REMARKS>> <PRE-OPERATION>
∨ ∨                              ∧ ∧ ∧

- PAGING (A NUMBER OF PAGE / THE TOTAL NUMBER OF PAGES)
- MEASUREMENT CATEGORY
- MEASUREMENT ITEM
- CALCULATION ITEM
- DOCTOR'S VIEW

FIG. 4A

REPORT(2/2)

TIS9.9 TIB9.9 TIC9.9 MI9.9
999                  96/05/11
A-HEART2   08:15:30AM
HT:175.0cm  BSA:1.77cm²
WT: 60.0kg   <ADULT>

☐ MITRAL VALVE

| | | |
|---|---:|---|
| CEAMP | 45.4 | (mm) |
| DEAMP | 26.0 | (mm) |
| CAAMP | 38.2 | (mm) |
| EPSS | 48.3 | (mm) |
| DESLP | 65.2 | (mm/s) |
| EFSLP | 277 | (mm/s) |
| CA/CE | 0.84 | |

☐ %STENOSIS

| | | |
|---|---:|---|
| DMAX1 | 56.3 | (mm) |
| DMIN1 | 32.3 | (mm) |
| DMAX2 | 52.7 | (mm) |
| DMIN2 | 28.4 | (mm) |
| AMAX1 | 752.0 | (mm²) |
| AMIN1 | 402.0 | (mm²) |
| AMAX2 | 402.5 | (mm²) |
| AMIN2 | 385.6 | (mm²) |
| D1%S | 42.8 | (%) |
| D1² %S | 67.2 | (%) |
| D2%S | 46.1 | (%) |
| D2² %S | 71.0 | (%) |
| A1%S | 46.5 | (%) |
| A2%S | 4.2 | (%) |

☐ DOPPLER   PG

| | | |
|---|---:|---|
| VP1 | 0.39 | (m/s) |
| VM1 | 0.10 | (m/s) |
| PG1 | 0.6 | (mmHg) |
| MPG1 | 0.3 | (mmHg) |
| VP2 | 0.25 | (m/s) |
| VM2 | 0.11 | (m/s) |
| PG2 | 0.2 | (mmHg) |
| MPG2 | 0.1 | (mmHg) |

<REMARKS> ∨ ∨ ∨                                                       ∧ ∧ ∧

FIG. 4B

|  |  |  |  | TIS9.9 TIB9.9 TIC9.9 MI9.9 |
|---|---|---|---|---|
|  |  |  |  | 999  96/05/11 |
|  |  |  |  | A-HEART2  08:15:30AM |
|  |  |  |  | HT:175.0cm  BSA:1.77cm² |
|  |  | REPORT(1/2) |  | WT: 60.0kg  <ADULT> |

| ☐ LV(SIMPSON) | | PHT1 | 240 | (ms) | CEAMP | 45.4 | (mm) |
|---|---|---|---|---|---|---|---|
| LVLD | 54.5 (mm) | MPG | 10.0 | (mmHg) | DEAMP | 26.0 | (mm) |
| VLAMD | 3.2 (cm²) | VP2 | −0.13 | (m/s) | CAAMP | 38.2 | (mm) |
| LVAPD | 2.8 (cm²) | VM2 | −0.09 | (m/s) | EPSS | 48.3 | (mm) |
| LVLS | 28.3 (cm²) | PHT2 | 182 | (ms) | DESLP | 65.2 | (mm/s) |
| LVAMS | 1.2 (cm²) | MPG2 | 20.1 | (mmHg) | EFSLP | 277 | (mm/s) |
| LVAPS | 2.0 (cm²) | | | | | | |
| HR | 63 | MVA | 91.7 | (mm²) | CA/CE | 0.84 | |
| | | MVA2 | 125.0 | (mm²) | | | |
| EDV | 12.8 (mL) | | | | ☐ %STENOSIS | | |
| ESV | 3.3 (mL) | ☐ AORTIC | | | | | |
| SV | 9.5 (mL) | | | | DMAX1 | 56.3 | (mm) |
| CO | 0.60 (L) | RVOTD | 69.6 | (mm) | DMIN1 | 32.3 | (mm) |
| EF | 0.74 | AOD | <32.2> | (mm) | DMAX2 | 52.7 | (mm) |
| SI | 5.4 | LAD | 55.4 | (mm) | DMIN2 | 28.4 | (mm) |
| CI | 0.34 | AVD | 28.0 | (mm) | AMAX1 | 752.0 | (mm²) |
| | | ET | 1040 | (ms) | AMIN1 | 402.0 | (mm²) |
| ☐ DOPPLER MVA | | | | | AMAX2 | 402.5 | (mm²) |
| | | LA/AO | <1.6> | | AMIN2 | 385.6 | (mm²) |
| VP1 | −0.11 (m/s) | | | | | | |
| VM1 | −0.10 (m/s) | ☐ MITRAL VALVE | | | D1%S | 42.8 | (%) |
| | | | | | D11%S | 67.2 | (%) |

<REMARKS> <PRE-OPERATION                                      >
                <                                                   >
                <                                                   >

FIG. 5A

```
                                    TIS9.9 TIB9.9 TIC9.9 MI9.9
                                      999              96/05/11
                                      A-HEART2    08:15:30AM
                                    HT:175.0cm  BSA:1.77cm²
              REPORT(2/2)           WT: 60.0kg    <ADULT>

D2%S    46.1  (%)
D22%S   71.0  (%)
A1%S    46.5  (%)
A2%S     4.2  (%)
────────────────
☐  DOPPLER PG

VP1     0.39  (m/s)
VM1     0.10  (m/s)
PG1     0.6   (mmHg)
MPG1    0.3   (mmHg)
VP2     0.25  (m/s)
VM2     0.11  (m/s)
PG2     0.2   (mmHg)
MPG2    0.1   (mmHg)

<REMARKS> <                                          >
          <                                          >
          <                                          >
```

FIG. 5B

ULTRASONIC MEASUREMENT APPARATUS

BACKGROUND OF THE INVENTION

The present invention relates to an ultrasonic measurement apparatus having the function of, with the use of an ultrasonic image, such as a B mode image (tissue cross-section image), M mode image and doppler mode image, measuring a point-to-point distance for instance, editing a result of measurement and of calculation in report form and displaying and printing it out.

Various apparatuses are known which use an ultrasonic wave for medical application. Their major application is to an ultrasonic diagnostic apparatus for diagnosing a cross-sectional image of the soft tissue of a living body with the use of the apparatus using an echo of an ultrasonic pulse wave. This type of diagnostic apparatus uses a non-invasive checking method and displays the cross-sectional image of the tissue and has its own unique features advantageous over other diagnostic apparatuses, such as the X-ray diagnostic apparatus, X-ray CT apparatus, MRI apparatus and nuclear-medicine diagnostic apparatus, that is, the features of being capable of real-time display, being compact and inexpensive, being free of X-ray exposure and safer and capable of bloodstream imaging by an ultrasonic doppler method.

For these reasons, such apparatus finds an extensive effective application in the field of the heart, abdomen, mammary glands and urinary organs as well as in the obstetric/gynecologic field. In particular, the heart's beats, as well as the aspect of the fetus's movement, can be obtained on a real-time display by a simple operation of applying an ultrasonic probe to a body surface of a human subject. Further, the apparatus can repeatedly check them more safely and can readily be moved along the bedside in a simpler way.

In view of such various advantages, the apparatus has recently been used not only to measure the sizes of the fetus, lesion, organ, etc., on a tissue's cross-sectional image (B mode) based on the point-to-point distance, circumferential length, area, capacity, etc., as have been practiced in the fields above but also to calculate the inner diameter of the heart's mitral valve and aortic valve and their retracting rate as well as a pressure comparison difference using a doppler mode, left ventricle's diastolic (systolic) volume, stroke volume, cardiac output and ejection fraction. In this way, the number of items to be measured is increased, so that more and more utility is obtained from the apparatus.

Of such ever-increasing measuring items, optional items are selected by the operator and the results of measurements and calculations, together with the titles of the measuring items, can be edited in report form, displayed on a CRT and printed out.

As set out above, a vast number of measuring items have been involved and several tens of pages are required in report form. As a result, in order to search for a specific item or items of measurement results in a report, it is necessary to frequently thumb through pages or effect page scrolling.

BRIEF SUMMARY OF THE INVENTION

It is accordingly an object of the present invention to provide an ultrasonic diagnostic apparatus which can reduce an operator's required operations and output results of measurements in a readily readable form.

At a measuring time, when at least one desired measurement category is selected from among a plurality of measurement categories associated with an ultrasonic image, at least one measurement item is selected from among a plurality of measurement items under the selected measurement category. Measurements corresponding to the selected measurement items are made sequentially. A title of those selected measurement items is inserted in a report. Since the title of those not-selected measurement items is not inserted in the report, a situation never occurs in which the actually measured items and measurement results are buried in a vast number of measurement items, making it difficult to find them. That is, it is possible to minimize the number of pages and, by doing so, easily review the full actual measurement items one at a time on one screen or one page and simply do this while scrolling fewer times on a display screen or eye-scanning the pages of the report as required.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 4A and 4B are views showing one form of a report edited by the present embodiment; and FIGS. 5A and 5B are views showing another form of a report edited by the present embodiment.

DETAILED DESCRIPTION OF THE INVENTION

Figure 1:
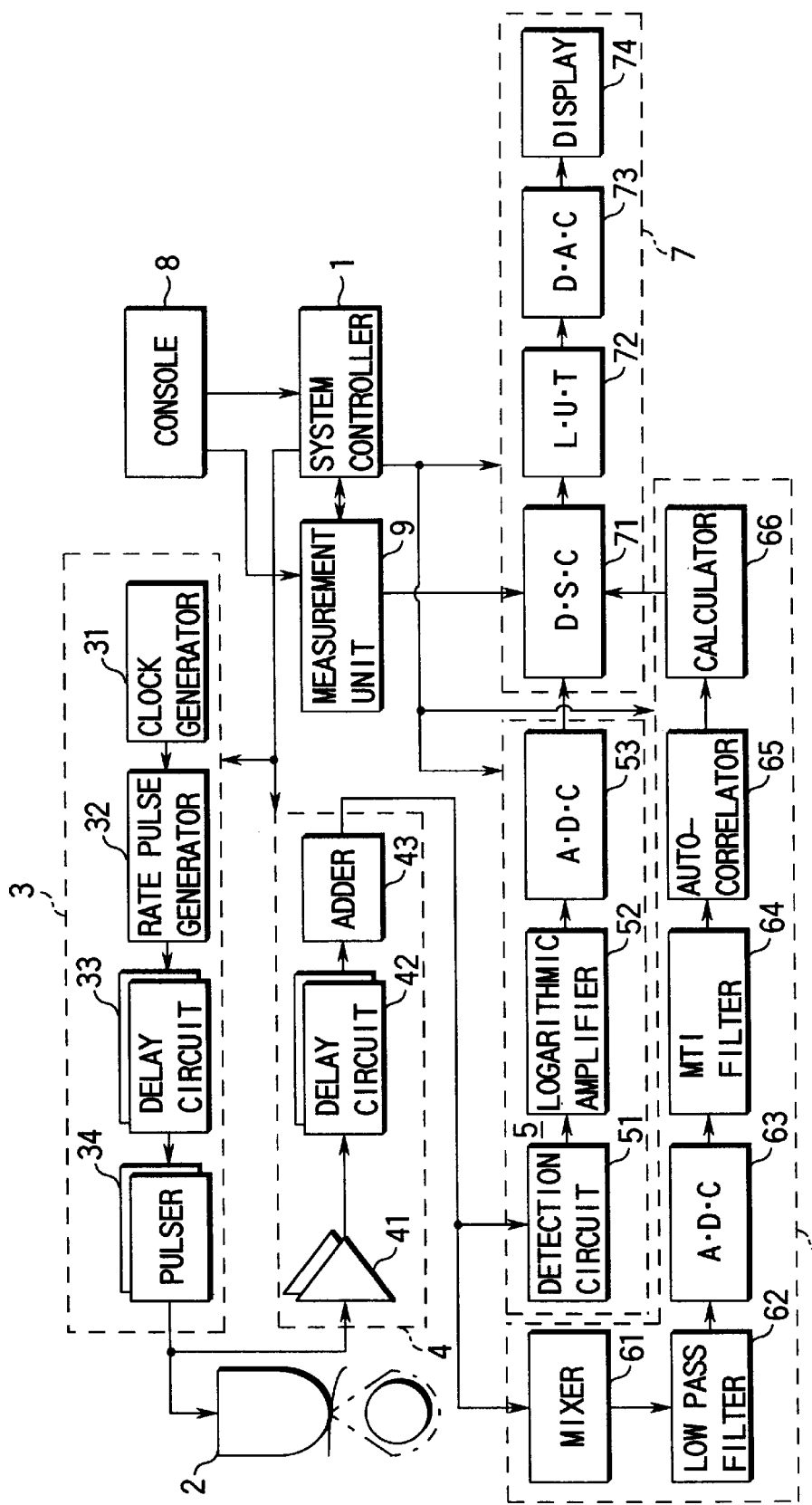
FIG. 1 is a block view showing an arrangement of an ultrasonic diagnostic apparatus according to a preferred embodiment of the present invention.

An ultrasonic diagnostic apparatus according to a preferred embodiment of the present invention will be explained below with reference to the accompanying drawings. FIG. 1 shows an arrangement of the ultrasonic diagnostic apparatus of the present invention. A system controller 1 constitutes a control center in the apparatus of the present embodiment. An ultrasonic probe 2, transmitting unit 3, receiving unit 4, B-mode processing unit 5, color doppler processing unit 6, display unit 7, console 8 and measuring unit 9 are provided under control of a system controller 1.

Although only the B-mode processing unit 5 functioning as a B mode and color doppler processing unit 6 as a color doppler mode (bloodstream color image) are restrictively shown in FIG. 1, the apparatus may be equipped with a unit operated in the imaging modes as will be set out below.

An M mode: a mode in which a cross-sectional image relating to one scanning line of the heart, etc., is arranged on a time base and it is possible to represent the motion of a portion of the heart's valve, etc., with a sequence of time.

A continuous wave doppler mode: a mode in which it is possible to analyze the spectrum of a doppler-shift frequency from echoes obtained through the continuous transmission of an ultrasonic wave to a human subject and, by doing so, to measure the state of a bloodstream on a scanning line, in detail, without involving any "aliasing" phenomenon as in a pulse doppler.

A pulse doppler mode: a mode also called a one-point doppler, in which a human subject is irradiated with a pulse wave of a given frequency and a time gate is applied to a corresponding echo obtained and, by doing so, it is possible to extract a doppler shift frequency relating to a point corresponding to a depth point at a corresponding time gate and measure, in detail, a state of a bloodstream on that point.

In the ultrasonic probe 2, a plurality of piezoelements are so arranged as to allow a reversible conversion between the ultrasonic signal and an electric signal. This type of probe 2 may optionally be selected from the group of a sector, linear, convex, etc., type.

The transmitting unit 3 comprises a clock generator 31, rate pulse generator 32, transmit delay circuit 33 and pulser 34 and is adapted to allow the ultrasonic wave to be properly transmitted from the ultrasonic probe 2. The rate pulse generator 32 is adapted to frequency-divide a clock signal from the clock generator 31 and to generate a rate pulse over a multi-channel. The transmit delay circuit 33 delays the rate pulse at each channel. The pulser 34 applies a voltage signal of a high frequency to a corresponding piezoelement of the probe 2 in synchronization with the rate pulse. It is to be noted that the frequency of the voltage signal is set to "$f_0$" in accordance with a resonant frequency of the piezoelement. The ultrasonic wave generated from the probe 2 is dispersed with the $f_0$ as a center.

The ultrasonic wave transmitted from the probe 2 to the human subject is echoed, at an acoustic impedance boundary, back to the probe 2. The amplitude of the echo reflects a difference of the acoustic impedance at the boundary. Further, the frequency of the ultrasonic wave is shifted, depending upon the velocity of a moving substance or unit, such as the blood cell or heart wall. For the B mode, the brilliance is allocated in accordance with the amplitude of the echo and displayed. For the color doppler, the doppler shift frequency is detected and the color and brilliance are allocated by properly combining the shift frequency (average frequency, dispersion and power).

The receiving unit 4 comprises a preamplifier 41, receive delay circuit 42 and adder 43 and is adapted to receive the echo. The receive delay circuit 42 delays, at each channel, an echo signal which is amplified by the preamplifier 41. The adder 43 adds the delayed echo signal. Through such delay and addition it is possible to generate one echo signal having a reception directionality.

In order to generate B-mode image data from the echo signal, the B-mode processing unit 5 comprises a detection circuit 51, logarithmic amplifier 52 and analog-digital-converter (A·D·C) 53. The detection circuit 51 detects an envelope signal from the echo signal. The logarithmic amplifier 52 logarithmically amplifies the envelope signal so as to compensate for the attenuation depth dependance. The analog-digital-converter 53 converts a logarithmically amplified envelope signal to a digital signal.

In order to generate color bloodstream data from the echo signal, the color doppler processing unit 6 comprises a mixer 61, lowpass filter 62, analog-digital-converter (A·D·C) 63, MTI filter 64, autocorrelator 65 and calculator 66. The mixer 61 and lowpass filter 62 take out a doppler shift frequency signal through their orthogonal phase detection of the echo signal. The analog-digital-converter 63 converts the doppler shift frequency signal to a digital signal. The MTI filter 64 eliminates, from a digitized doppler shift frequency signal, a low frequency component (clatter component) corresponding to the organ wall of a relatively slow motion and extracts a high frequency component corresponding to the blood cell of relatively rapid motion.

The autocorrelator 65 finds an average frequency and dispersion by frequency-analyzing the extracted high-frequency component, at a time region, with the use of the autocorrelation function. The calculator 66 calculates an average velocity, dispersion and power from the output of the autocorrelator 65.

In order to properly combine together the B mode image data generated at the B mode processing unit 5 and color doppler data generated at the color doppler processing unit 6, prepare display data and display it, the display unit 7 comprises a digital scan converter (DSC) 71, look-up table (LUT) 72, digital-analog converter (D·A·C) 73 and color display 74. The digital-scan-converter 71 converts an image data array from an ultrasonic scanning system to a television scanning system. The look-up table 72 converts the image data to RGB type display data. The digital-analog-converter 73 converts the display data to an analog signal and the display 74 displays an analog version of display data.

Figure 2:
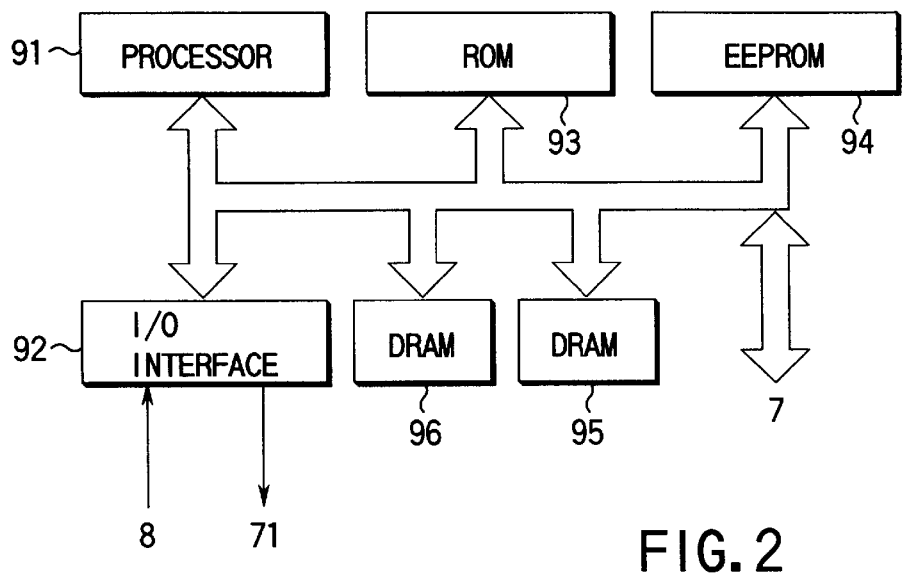
FIG. 2 is a block diagram showing a measurement unit in FIG. 1.

The measuring unit 9 constitutes a featuring constituent unit of the present invention which has a function of effecting a measurement relating to the ultrasonic image and function of editing results of such measurements in a report. FIG. 2 shows a practical form of a measuring unit 9. In order to implement a software program having these functions, the measuring unit 9 comprises a processor 91, data/control bus 90, input/output (I/O) interface 92 relative to the console 8 and digital scanning converter 71, ROM 93, EEPROM 94 and DRAMs 95, 96.

In order to handle several kinds of measuring items, the ROM 93 keeps several kinds of measuring programs and edit program. The ROM 93 keeps text data relating to the measuring categories necessary for the editing of the report and titles of the measuring items as well as the priority with which the items of the measuring items are arranged. Further, the processor 91 performs measuring (calculation) processing corresponding to the respective measuring items in accordance with the measuring program and edit program and the result of measuring is edited in the report. The edit program allows the order of the measuring items on the report to be freely changed by the user. The order of the changed measuring items can be stored in the EEPROM (electrical erasable and programmable ROM) 94 and can be re-displayed at the next measuring time.

As an example of measuring items, there are the diameter, circumference length, cross-sectional area and capacity of a fetal head, the diameter, circumference length, cross-sectional area and capacity of a lesion, the diameter, circumference length, cross-sectional area and capacity of the organ, the diameter and retracting velocity of the mitral valve, the internal diameter and retracting velocity of the aortic valve, the pressure comparison difference, the left ventricle's end diastolic (systolic) capacity, the stroke volume, the cardiac output and the ejection fraction.

Many of these items can be classified into several measurement categories. As one category, there are an LV (left venticle), AORTIC (aorta), MITRAL VALVE (mitral valve) and STENOSIS (stenosis).

By operating the console 8 and starting the measuring program, the measuring category list is displayed on a TCS (touch command screen) display 74. From the measurement category list the operator selects at least one measuring category. Then, the measuring item list for the selected measurement category is displayed on the display 74. From the measuring item list the operator selects at least one measuring item. Such operations are repeated on all the selected categories and, by doing so, the setting of the measurement list is completed.

Here, it is assumed that three measurement categories (A), (B) and (C) are selected and that three measurement items (a-1), (a-2), (a-3) are selected from the measurement category (A), two measurement items (b-1), (b-2) from the measurement category (B) and four measurement items (c-1), (c-2), (c-3), (c-4) from the measurement category (c).

Figure 3:
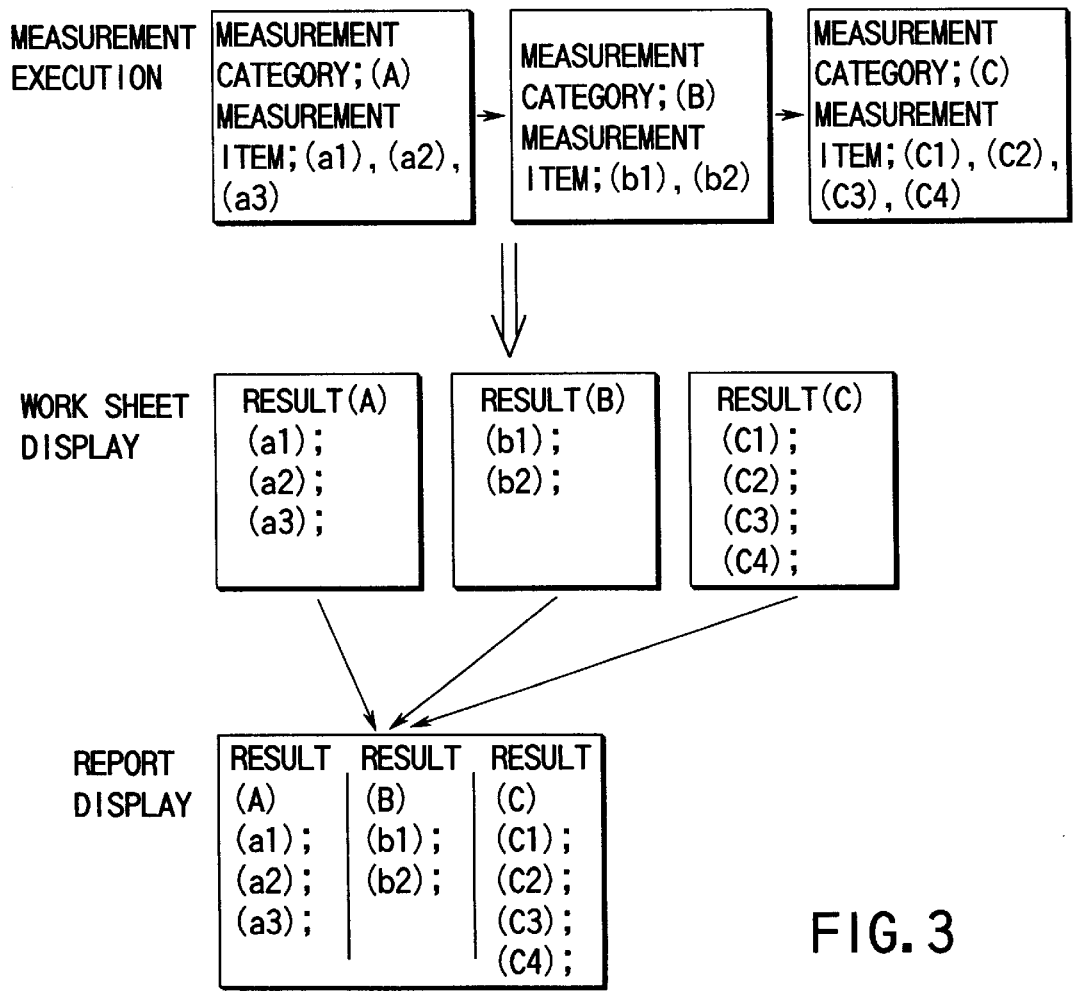
FIG. 3 is a view for explaining a flow from the effecting of measurement until results of measurements are edited in a report.

As shown in FIG. 3, measurements are sequentially carried out in accordance with the order of selection. That is, measuring processing is sequentially effected first on the measurement items (a-1), (a-2) and (a-3) under the first selected category (A), then on the measurement items (b-1) and (b-2) under the next category (B) and then (c-1), (c-2), (c-3) under the following category (c). And finally the measuring processing is effected on the finally selected measurement item (c-4). Further, the execution order of the measurement is not necessarily dependent upon the order of selection. For example, the measurements sequentially may be executed based on the order parameters initially given to each item.

It is to be noted that, for the respective measuring processing, their own information is required. As the information thus required, in the case of the "diameter" for instance, two opposite-angle points are designated by the operator via the console 8 and, in the case of the "circumference length", the outline of a symmetric region is traced by the operator via the console 8.

When the measuring processing is all done on the selected measurement items, the edit program is started, a corresponding work sheet is prepared and it is displayed on a display 74. Only the title of those selected/actually measured items (measurement items) and results of measurements are arranged on the work sheet in a normal order, or a reverse order, of the measurements. Those unselected or those actually not-measured items (measurement items) are eliminated from the list on the work sheet. The list data, being under a different category, is treated as a new page list.

Upon review of the work sheet, it is possible for the operator to change the order of the measurement items as required, such as re-sorting the pages or changing the order of measuring items in the same page. The order thus changed is stored in the EEPROM 94 and is applied at the next time of measurement.

If the operator, looking up the work sheet, feels that the results of measurements are low in reliability, then he or she can instruct the attendant remeasure, or to add new measurement items. The measurement items thus re-measured or added, after being measured at a final stage, are arranged at the head or end of the list.

The measurement items and results of such measurements are, as shown in FIGS. 4A, 4B, re-arranged, listed and edited, on the report, in accordance with the order of measurements or change of the order. The report form is comprised of at least one page and allows new pages to be added thereto in accordance with the number of measurement categories and of the measurement items. At the top of the respective page, the attaching information is inserted, such as the name, height, weight and checkup date. At the bottom of the respective page, a doctor's opinion is written. The relatively-wide intermediate area between the top and bottom of the page is separated into, for example, three columns, one column for the title of the measurement category, another column for the measurement items, and the third column for the results of measurements.

Only the list of the title of the measurement items corresponding to those selected/actually made measurements, as well as the results of such measurements, is written on the columns. Unlike the conventional case, those not-selected/ actually not-measured items are neither listed nor written on the report. The title of the listed measurement items and results of the measurements are vertically arranged along the columns in accordance with the order (or the reverse order) of the measurements or the changed order on the work sheet. Although, in FIGS. 4A, 4B, under a different category a different column is used, the measurement items and results of the measurements may be arranged, instead, in a closely continuous way as shown in FIGS. 5A, 5B.

The report is displayed and printed out.

In the present embodiment, those actually measured/not measured items are not fully written on the report with the not-actually measured item as a blank, that is, only those actually measured items are inserted on the report without leaving those not-actually measured items blank. As a result, there never occurs such a situation that the measured items and results of measurements are buried in a vast number of measured items, thus making it difficult to find a searching item. That is, it is possible to minimize the number of pages on the report and, by doing so, to easily review the full actual measurement items all at a time on one screen or one sheet or do this while being scrolled at somewhat fewer times on the display or eye-scanning the pages of the report. Further, since the order of the list on the measurement items and on results of the measurements can be freely changed, the list can very easily prepared on the report in an easily readable form.

Although, in the above-mentioned explanation, the actual measurement items are arranged in the order of the actual measurements, it may be possible to arrange the actual measurement items in their preferential order instead of the order of their measurement.

Various changes or modifications of the present invention can be made without departing from the spirit and scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. An ultrasonic diagnostic apparatus comprising:
   means for generating an ultrasonic image corresponding to an interior of a subject by scanning the interior of the subject with an ultrasonic wave and for displaying it;
   means for selecting at least one desired category from among a plurality of measurement categories associated with the ultrasonic image and for selecting at least one measurement item from among a plurality of measurement items under the selected measurement category;
   means for effecting measurements corresponding to the selected at least one measurement item sequentially to obtain measurement results;

means for editing a title of the selected at least one measurement item and the measurement results in a report form; and means for outputting the report;

wherein the means for editing is adapted to insert the title of the selected at least one measurement item and the measurement results in the report and omit titles of measurement items other than the selected at least one measurement item from the report.

2. The apparatus according to claim 1, wherein the means for editing arranges the title of the selected at least one measurement item and the measurement results in accordance with an execution order of the measurements.

3. The apparatus according to claim 1, wherein the means for editing arranges the title of the selected at least one measurement item and the measurement results in an order corresponding to a reverse order of execution of the measurements.

4. The apparatus according to claim 1, wherein the means for editing arranges the title of remeasured items and remeasurement results in accordance with an order of execution of a remeasurement.

5. The apparatus according to claim 1, wherein the means for editing arranges the title of the selected at least one measurement item and the measurement results in accordance with priorities defined for the selected at least one measurement item respectively.

6. The apparatus according to claim 1, wherein the means for editing is provided so as to rearrange the order of the plurality of measurement items in accordance with the operation of the means for selecting.

7. The apparatus according to claim 6, wherein the means for editing is provided so as to store the rearranged order in a memory and arrange the plurality of measurement items in accordance with the stored rearranged order when a next report of data is prepared.

8. The apparatus according to claim 1, wherein the means for editing divides the report into a plurality of columns and allocates the title of the selected at least one measurement item under a different measurement category in a different column for each selected one of the at least one desired category.

9. The apparatus according to claim 1, wherein the means for editing arranges the title of the selected at least one measurement item and measurement results closely together in a continuous form.

* * * * *